United States Patent [19]
Lundbeck et al.

[11] Patent Number: 5,834,482
[45] Date of Patent: Nov. 10, 1998

[54] HETEROCYCLIC CHEMISTRY

[75] Inventors: Jane Marie Lundbeck, Glostrup; Birgitte Soekilde, Vaerloese; Per Olaf Huusfeldt, Koebenhavn K, all of Denmark

[73] Assignee: Novo Nordisk A/S, Bagsvaerd, Denmark

[21] Appl. No.: 945,046

[22] PCT Filed: May 1, 1996

[86] PCT No.: PCT/DK96/00198

§ 371 Date: Oct. 21, 1997

§ 102(e) Date: Oct. 21, 1997

[87] PCT Pub. No.: WO96/34865

PCT Pub. Date: Nov. 7, 1996

[30] Foreign Application Priority Data

May 5, 1995 [DK] Denmark ................................. 0520/95

[51] Int. Cl.⁶ .......................... C07D 471/04; A61K 31/44
[52] U.S. Cl. ................................. 514/292; 546/86; 546/87
[58] Field of Search .......................... 546/86, 87; 514/292

[56] References Cited

U.S. PATENT DOCUMENTS 4,539,407 9/1985 Stack et al. ............................... 546/87

*Primary Examiner*—Alan L. Rotman
*Attorney, Agent, or Firm*—Steve T. Zelson; Carol E. Rozek

[57] ABSTRACT

A compound of formula (I). The present invention relates to therapeutically active β-carboline derivatives, a method of preparing the same and to pharmaceutical compositions comprising the compounds. The novel compounds are useful in treating a central nervous system ailment related to the inhibition of GABA uptake via the GAT-4 subtype carrier.

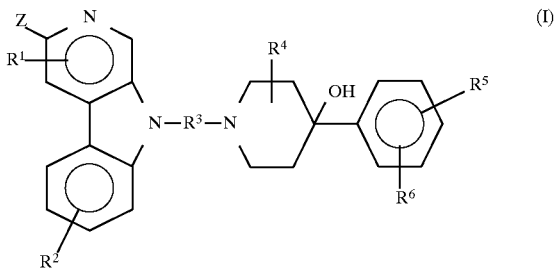

7 Claims, No Drawings

HETEROCYCLIC CHEMISTRY

CROSS-REFERENCE TO RELATED APPLICATIONS

This application is a 35 U.S.C. 371 national application of PCT/DK96/00198 filed May 1, 1996 and claims priority under 35 U.S.C. 119 of Danish application 0520/95 filed May 5, 1995, the contents of which are fully incorporated herein by reference.

FIELD OF THE INVENTION

The present invention relates to novel substituted β-carboline derivatives, to methods for their preparation, to pharmaceutical compositions containing them and to their use in the clinical treatment of abnormal functioning of the γ-aminobutyric acid neurotransmission system.

BACKGROUND OF THE INVENTION

γ-Aminobutyric acid (GABA) is the major inhibitory neurotransmitter in the central nervous system (CNS) (for review see Enna, 1983, Biochem. Pharmacol., 30, 907–15; Enna and Mohler, 1987, Raven Press, New York, 265–79; Lloyd and Morselli, 1987, Medical Biology, 65, (2–3), 159–65; Krogsgaard-Larsen, 1988, Medical Res. Reviews, 8, 1, 27–56; Schwartz, 1988, Biochem. Pharmacol. 27, 3369–76). GABA has been estimated to be present in 60–70% of all synapses within the CNS (Fahn, 1976, Raven Press, New York, 169–83). A reduction in GABA neurotransmission has been implicated in the etiology of a variety of neurological disorders including epilepsy (Krogsgaard-Larsen et al., 1988, Medical Res. Reviews, 8, 1, 27–56; Löscher, 1985, Epilepsy and GABA Receptor Agonists: Basic and Therapeutic Research. L.E.R.S. Monograph. Vol. 3, G. Bartholoni, L. Bossi, K. G. Lloyd, P. L. Morselli (Eds.), Raven Press, New York, 109–18); Enna, 1981, Biochem. Pharmacol., 30, 907–14 and Neuropharmacology of Central Nervous System GABA and Behavioral Disorders, G. Palmer (Ed.). Academic Press, New York 1981, 507–25; Rebak et al., 1979, Science, 205, 211–13; Ross and Craig, 1981, J.Neurochem. 36, 1006).

The GABA uptake system has traditionally been classified as either neuronal or glial GABA uptake carriers, on the basis of pharmacological selectivity for specific GABA uptake inhibitors (for review see: Krogsgaard-Larsen, 1988, Medical Res. Reviews, 8, 1, 27–56; Schousboe et al., 1991, GABA Mechanisms in Epilepsy, G. Tunnicliff, B. U. Raess (Eds.) Wiley-Liss, New York, 165–87).

Several investigators (Gaustella et al., 1990, Science, 249, 1303–1306; Clark et al., 1992, Neuron 9, 337–348; Borden et al., 1992, J.Biol. Chem. 267, 21098–21104; Liu et al., 1993, J.Biol.Chem. 268, 2106–2112) have recently cloned, and sequenced, four subtypes of the rat and mouse GABA uptake carrier, whose pharmacology cannot be totally explained by the traditional neuronal and glial GABA uptake carriers. Gaustella et al., (1990, Science, 249, 1303–1306) and Nelson et al. (1990, FEBS Lett. 269, 181–184) reported on the cloning of GAT-1, which appears to be a neuronal GABA uptake carrier due to its high sensitivity to nipecotic acid (Gaustella et al., 1990, Science, 249, 1303–1306), and lipophilic nipecotic acid based compounds and distribution within the central nervous system (CNS) (Radian et al., 1990, J.Neurosci. 10, 1319–1330; Mabjeesh et al., 1992, J.Biol.Chem. 267, 2563–68). GAT-1 is not present outside the CNS (Nelson et al., 1990, FEBS Lett. 269, 181–184; Liu et al., 1992, FEBS. Lett. 305, 110–114). GAT-2 was initially cloned by Lopez-Corruera (1992, J.Biol.Chem. 267, 17491–17493) and is present in the CNS, kidney and liver, and has a pharmacology resembling the glial GABA uptake carrier characterized in primary cell culture. GAT-3 which was initially cloned by Liu et al., (1993, J.Biol.Chem. 267, 2106–2112), appears to be under develop mental control, as GAT-3 mRNA is highly expressed in neonatal brain, but weakly expressed in adult brain. GAT-3 is also present in kidney and liver. GAT-4 (Liu et al., 1993, J.Biol.Chem. 268, 2106–2112; also termed GAT-B by Clark et al., (1992, Neuron 9, 337–348) and GAT-3 by Borden et al., (1992, J.Biol.Chem. 267, 21098–21104)), cDNA hybridized only in the CNS, and the mRNA for GAT-4 is highly enriched in the brain stem, but not present in the cerebellum or cerebral cortex. While GAT-4 has been shown to transport β-alanine, it appears to have neuronal localization (Clarke et al., 1992, Neuron 9, 337–348).

The distribution of GAT-1, closely resembles the previously reported distribution of $^3$H-Tiagabine receptor autoradiography (Suzdak et al., 1994, Brain Research, 647(2), 231–41), as would be expected due to the high affinity of lipophilic nipecotic acid based GABA uptake inhibitors for the GAT-1 transporter (Clarke et al., 1992, Neuron 9, 337–348). While in situ hybridization has revealed the presence of GAT-4 mRNA in the CNS, there has been no direct demonstration of a discretely localized neuronal GABA uptake carrier, which is not sensitive to lipophilic nipecotic acid based GABA uptake inhibitors.

The inhibition of GABA uptake results in enhanced availability of this inhibitory neurotransmitter in the synaptic cleft and thus to increased GABA'ergic activity. Increased GABA'ergic activity can be useful in the treatment, for example of anxiety, pain and epilepsy, as well as muscular and movement disorders (see, for example, P. Krogsgaard-Larsen et al., Progress in Medicinal Chemistry, 1985, 22, 68–112).

A well-known and potent inhibitor of GABA uptake from the synaptic cleft into presynaptic nerve terminals and glial cells is, for example, 3-piperidinecarboxylic acid (nipecotic acid). However, being a relatively polar compound and therefore unable to cross the blood-brain barrier, 3-piperidinecarboxylic acid itself has found no practical utility as a drug.

In U.S. Pat. No. 4,383,999 and U.S. Pat. No. 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as inhibitors of GABA uptake. EP 221572 claims that 1-aryloxyalkylpyridine-3-carboxylic acids are inhibitors of GABA uptake.

According to Yunger, L. M. et al., J.Pharm.Exp.Ther. 1984, 228, 109, N-(4,4-diphenyl-3-buten-1-yl)nipecotic acid (designated SK&F 89976A), N-(4,4-diphenyl-3-buten-1-yl)guvacine (designated SK&F 100330A), N-(4,4-diphenyl-3-buten-1-yl)-homo-β-proline (designated SK&F 100561) and N-(4-phenyl-4-(2-thienyl)-3-buten-1-yl) nipecotic acid (designated SK&F 100604J) are orally active inhibitors of GABA uptake. These data are summarized in Krogsgaard-Larsen, P. et al., Epilepsy Res. 1987, 1, 77–93.

The above cited references all disclose compounds inhibiting the uptake of GABA via the GAT-1 subtype carrier.

U.S. Pat. No. 4,539,407 discloses β-carboline-3-carboxylate ester derivatives having anticonvulsant activity.

The present invention is directed to identifying novel compounds with affinity for the neuronal subtype of the GABA uptake carrier whose pharmacology resembles that of GAT-4.

DESCRIPTION OF THE INVENTION

The present invention relates to novel substituted β-carboline derivatives of formula I

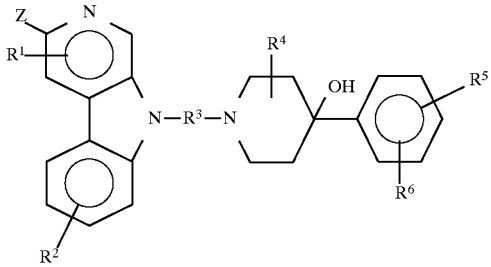

wherein $R^1$ and $R^2$ independently are hydrogen, halogen, hydroxy, nitro, —$(CH_2)_n$—(C=O)—$(CH_2)_m CH_3$, —$NR^9 R^{10}$, —$SONR^{11} R^{12}$, —$COOR^{13}$, —$CONR^{14} R^{15}$, $C_{1-6}$-alkyl, $C_{1-6}$-alkoxy, trifluoromethyl or trifluoromethoxy wherein $R^9$, $R^{10}$, $R^{11}$, $R^{12}$, $R^{13}$, $R^{14}$ and $R^{15}$ independently are hydrogen, $C_{1-6}$-alkyl, $C_{2-6}$-alkenyl or $C_{2-6}$-alkynyl, and wherein n and m independently are 0, 1, 2, 3 or 4; and $R^3$ is $C_{1-5}$-alkylene optionally substituted with one or two $C_{1-6}$-alkyl or $C_{3-7}$-cycloalkyl, $C_{2-5}$-alkenylene or $C_{2-5}$-alkynylene or

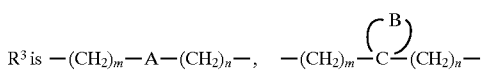

or

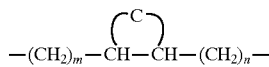

wherein A is $C_{3-7}$-cycloalkylene and B is $C_{1-5}$-alkylene and C is $C_{1-5}$-alkylene and m and n independently are 0, 1 or 2; and $R^4$ is hydrogen or $C_{1-6}$-alkyl; and $R^5$ and $R^6$ independently are hydrogen, halogen, hydroxy, nitro, —$NR^{16} R^{17}$, —$COOR^{18}$, $C_{1-6}$-alkyl, $C_{1-6}$-alkoxy, trifluoromethyl or trifluoromethoxy wherein $R^{16}$, $R^{17}$ and $R^{18}$ independently are hydrogen, $C_{1-6}$-alkyl, $C_{2-6}$-alkenyl or $C_{2-6}$-alkynyl; and Z is

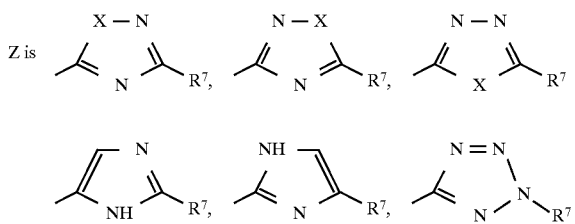

wherein X is —NH—, oxygen or sulphur; and $R^7$ is hydrogen, $C_{1-6}$-alkyl, $C_{2-6}$-alkenyl, $C_{2-6}$-alkynyl, phenyl, $C_{3-7}$-cycloalkyl, —$OR^8$ or —$SR^8$ wherein $R^8$ is hydrogen or $C_{1-6}$-alkyl; or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallization of suitable salts.

The compounds according to the invention may optionally exist as pharmaceutically acceptable acid addition salts.

Examples of such salts include inorganic and organic acid addition salts such as hydrochloride, hydrobromide, sulphate, phosphate, acetate, phthalate, fumarate, maleate, citrate, lactate, tartrate, oxalate, or similar pharmaceutically acceptable inorganic or organic acid addition salts, and include the pharmaceutically acceptable salts listed in Journal of Pharmaceutical Science, 66, 2 (1977) which are hereby incorporated by reference.

Alkyl, alkenyl and alkynyl are intended to mean straight or branched alkyl, alkenyl or alkynyl chains.

The compounds of formula I have a greater lipophilicity—and thus a greater availability to the brain—as well as a far higher affinity to the GABA uptake sites than the parent compounds without the β-carboline moiety.

It has been demonstrated that the novel compounds of formula I which inhibit the uptake of GABA from the synaptic cleft possess useful pharmacological properties in the central nervous system, in that they cause a selective enhancement of GABA'ergic activity. Compounds of formula I may be used to treat for example, pain, anxiety, extrapyrimidinal dyskinesia, epilepsy and certain muscular and movement disorders. They are also useful as sedatives, hypnotics and antidepressants.

The invention also relates to a method of preparing the above mentioned compounds of formula I. These methods comprise:

Method A:

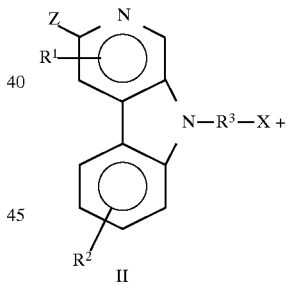

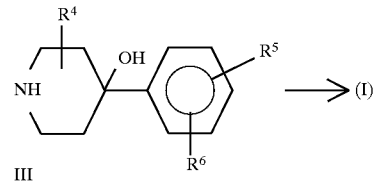

A compound of formula II wherein $R^1$, $R^2$, $R^3$ and Z are as defined above and X is a suitable leaving group such as halogen, p-toluene sulphonate or mesylate may be reacted with an azaheterocyclic compound of formula III wherein $R^4$, $R^5$ and $R^6$ are as defined above. This alkylation reaction may be carried out in a suitable solvent such as acetone, dibutylether, 2-butanone, tetrahydrofuran, methylisobutyl ketone, methylisopropyl ketone, toluene, benzene or DMF in the presence of a base e.g. potassium carbonate, sodiumhydride or potassium tert.-butoxide at a temperature up to reflux for the solvent used for e.g. 1 to 200 h.

Method B:

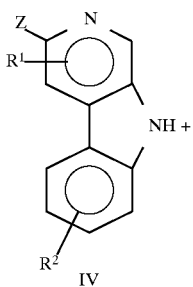

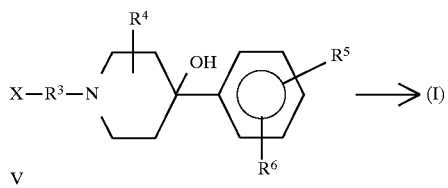

A compound of formula IV wherein $R^1$, $R^2$ and Z are as defined above may be reacted with an azaheterocyclic compound of formula V wherein $R^3$, $R^4$, $R^5$, $R^6$ and X are as defined above. This alkylation may be carried out in a suitable solvent as defined above in the presence of a base as defined above and a catalyst e.g. an alkali metal iodide at a temperature up to reflux for the solvent used for e.g. 1 to 200 h.

Method C:

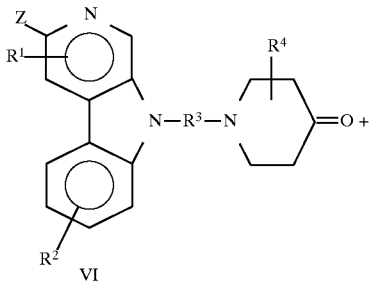

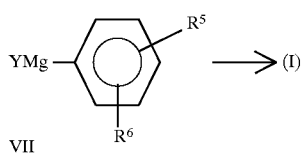

An azaheterocyclic ketone of formula VI wherein $R^1$, $R^2$, $R^3$, $R^4$ and Z are defined as above may be reacted with a Grignard reagent of formula VII wherein $R^5$ and $R^6$ are as defined above and Y is chloro, bromo or iodo. This reaction may be carried out in a suitable solvent such as diethylether, THF, toluene or benzene at a suitable temperature up to reflux temperature for the solvent used for e.g. 1 to 5 h.

Compounds of formula II may readily be prepared according to the procedure described in EP 0 130 141 or EP 0 161 574.

Pharmacological Methods $^3$H-GABA uptake was measured by a modification of the method of Fjalland et al., (1978). A crude membrane preparation was prepared from selected brain areas by homogenization in 20 ml of ice-cold 0.32M sucrose with a hand driven teflon/glass Potter-Elvehjem homogenizer. homogenate was centrifuged at 4° C. for 10 min. at 1000×g, and the pellet was discarded. The supernatant was recentrifuged at 4° C. for 20 min. at 20.000×g. The pellet was then homogenized in 50 volumes 0.32M sucrose. To 300 µl uptakebuffer (200 nM NaCl, 15.3 mM KCl, 6.67 mM MgSO$_4$, 3.83 mM CaCl$_2$, 16.67 mM glucose, 66.67 mM Tris, pH 7.5 at 30° C.) was added 1-(2-(((diphenylmethylene)amino)oxy)ethyl)-1,2,5,6-tetrahydro-3-pyridinecarboxylic acid (NNC 05–0711) (1 mM final concentration), 100 µl test substance and 50 µl tissue suspension. The sample were mixed and incubated at 30° C. for 8 min. Then $^3$H-GABA (0.9 nM final concentration) and unlabelled GABA (25 nM final concentration) was added, and the incubation was continued for an additional 8 min. The reaction was terminated by rapid filtration through Whatman GF/F glass fiber filters under vacuum. The filters were then washed twice in 10 ml of ice-cold isotonic saline, and the tritium trapped on the filters was quantified by conventional scintillation spectroscopy. Non-GABA uptake carrier mediated uptake of $^3$H-GABA was determined in the presence of 500 µl nipecotic acid.

Value for non-GABA uptake carrier mediated uptake of $^3$H-GABA for some representative compounds are recorded in Table I.

TABLE I

Non-GABA uptake carrier mediated uptake of $^3$H-GABA.

| Compound No. | IC$_{50}$ (nM) in vitro |
| --- | --- |
| 4 | 932 |
| 7 | 1089 |
| 10 | 1439 |
| 15 | 6375 |
| 20 | 5385 |
| 24 | 4692 |
| 26 | 1641 |
| 28 | 1241 |

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

The compounds of formula I may be administered in pharmaceutically acceptable acid addition salt form or where possible as a metal or a lower alkylammonium salt.

This invention also relates to pharmaceutical compositions comprising a compound of formula I or a pharmaceutically acceptable salt thereof and, usually, such compositions also contains a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely, but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispended in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet, which may be prepared by conventional tabletting techniques contains:

| Core: | |
|---|---|
| Active compound (as free compound or salt thereof) | 100 mg |
| Colloidal silicon dioxide (Aerosil, TM) | 1.5 mg |
| Cellulose, microcryst. (Avicel, TM) | 70 mg |
| Modified cellulose gum (Ac-Di-Sol, TM) | 7.5 mg |
| Magnesium stearate | |
| Coating: | |
| HPMC | approx. 9 mg |
| *Mywacett, TM 9-40 T | approx. 0.9 mg |

*Acylated monoglyceride used as plasticizer for film coating.

The route of administration may be any route, which effectively transports the active compound to the appropriate or desired site of action, such as oral or parenteral e.g. rectal, transdermal, subcutaneous, intravenous, intraurethral, intramuscular, topical, intranasal, ophthalmic solution or an ointment, the oral route being preferred.

EXAMPLE

The process for preparing compounds of formula I is further illustrated in the following examples which however are not to be construed as limiting.

Hereinafter, DMF is N,N-dimethylformamide, TEA is triethylamine, TLC is thin layer chromatography and THF is tetrahydrofuran, $CDCl_3$ is deuterio chloroform and $DMSO$-$d_6$ is hexadeuterio dimethylsulfoxide. The structures of the compounds are confirmed by either elemental analysis or NMR, where peaks assigned to characteristic protons in the title compounds are presented where appropriate. NMR shifts (δ) are given in parts per million (ppm). M.p. is melting point and is given in °C. Column chromatography was carried out using the technique described by W. C. Still et al, J. Org. Chem. 1978, 43, 2923–2925 on Merck silica gel 60 (Art. 9385). Compounds used as starting materials are either known compounds or compounds which can readily be prepared by methods known per se.

Example 1
(9H-β-Carbolin-3-yl)-imidazol-1-ylmethanone (Compound 1)

To a suspension of 9H-β-carboline-3-carbocylic acid (1.98 g, 9.3 mmol) in a mixture of anhydrous DMF (100 mL) and anhydrous THF (100 mL), 1,1'-carbonyldiimidazole (1.60 g, 10 mmol) was slowly added. The reaction mixture was stirred under a nitrogen atmosphere for 7 days. The solvents were removed in vacuo, the solid residue washed with water, and dried in vacuo to give the title compound (1.12 g, 45%). White solid, M.p. >280° C.

Example 2
3-(3-Ethyl-1,2,4-oxadiazol-5-yl)-9H-β-carboline (Compound 2)

To a solution of Compound 1 (1.05 g, 4 mmol) in a mixture of toluene (50 mL) and DMF (50 mL), N-hydroxypropanimidamide (0.53 g, 6 mmol) was added. The resulting mixture was heated at 140°–150° C. for 7 h, and stirring continued for 3 days at room temperture. The solvents were removed in vacuo, and the oily residue precipitated from water. The white solid (1.0 g) was dried and submitted to column chromatography on silica gel with $CH_2Cl_2$/methanol(9:1) as eluent. This afforded the title compound (0.6 g, 56%). M.p. 146°–149° C.

Example 3
9-(3-Chloro-1-propyl)-3-(3-ethyl-1,2,4-oxadiazol-5-yl)-9H-β-carboline (Compound 3)

To a solution of Compound 2 (0.73 g, 2.8 mmol) in anhydrous DMF (100 mL), sodium hydride (60% in mineral oil, 0.13 g, 3.3 mmol) was carefully added. The resulting mixture was stirred at room temperature for 30 min, until hydrogen evolution had ceased. The reaction mixture was slowly added to a solution of 1-bromo-3-chloropropane (0.52 g, 3.3 mmol) in anhydrous DMF (150 mL). The resulting mixture was stirred at room temperature for 12 h. The solvents were removed in vacuo to give a yellow solid (1.59 g). The residue was dissolved in acetone, filtered and the filtrate concentrated in vacuo, giving the title compound (1.07 g, 100%). $^1H$- and $^{13}C$-NMR revealed that the crude product was a mixture of the bromo and chloro isomers in the ratio 70:8. The crude product was used without further purification.

Example 4
1-(3-(3-(3-Ethyl-1,2,4-oxadiazol-5-yl)-9H-β-carbolin-9-yl)-1-propyl)-4-phenylpiperidin-4-ol (Compound 4)

To a solution of Compound 3 (1.0 g, 3 mmol) in anhydrous DMF (50 mL), 4-phenylpiperidin-4-ol (0.63 g, 3.5 mmol) and TEA (1 mL) were added. The resulting mixture was heated at 85° C. for 76 h under a nitrogen atmosphere. The solvent was removed in vacuo, and the solid residue was submitted to column chromatography on silica gel with $CH_2Cl_2$/methanol (9:1) as eluent. The purified compound was precipitated as the hydrochloride, giving the title compound (0.6 g, 36%) as an yellow solid. M.p. 169°–170° C.

Example 5
3-(3-Cyclopropyl-1,2,4-oxadiazol-5-yl)-9H-β-carboline (Compound 5)

To a solution of sodium ethoxide, prepared from sodium metal (0.6 g, 26 mmol) and anhydrous ethanol (50 mL), cyclopropylmethanimidamide (1.67 g, 16 mmol) and 9H-β-carboline-3-carboxylic acid ethyl ester (2.0 g, 8.0 mmol) were added. Toluene (50 mL) was added and the resulting mixture was heated to 120°–130° C. The ethanol and water formed during the reaction were removed by azeotropic distillation. The reaction was complete after 30 min. The solid was filtered from the reaction mixture, washed with water and dried. This afforded the title compound (1.15 g, 52%) as an yellow solid. M.p. 256°–257° C.

Example 6
9-(3-Chloro-1-propyl)-3-(3-cyclopropyl-1,2,4-oxadiazol-5-yl)-9H-β-carboline (Compound 6)

The compound was synthesized by mixing (Compound 5) (1.0 g, 3.6 mmol), NaH (0.22 g, 4.3 mmol) and 1-bromo-3-chloropropane (0.68 g, 4.3 mmol)in DMF, in the same manner as illustrated in example 3, to give the title compound (0.76 g, 63%) as a white solid. M.p. 165°–169° C.

Example 7
1-(3-(3-(3-Cyclopropyl-1,2,4-oxadiazol-5-yl)-9H-β-carbolin-9-yl)-1-propyl)-4-phenylpiperidin-4-ol hydrochloride (Compound 7)

The compound was synthesized by mixing (Compound 6) (0.76 g, 2.2 mmol), 4-phenylpiperidin-4-ol (0.48 g, 2.7 mmol), TEA (0.55 g, 5.4 mmol) in DMF, in the same manner as illusterated in example 3. The compound was isolated as the hydrochloride (0.15 g, 12%) as an yellow solid. M.p. 184°–185° C.

Example 8
3-(3-Phenyl-1,2,4-oxadiazol-5-yl)-9H-β-carboline (Compound 8)

The compound was synthesized by mixing 9H-β-carboline-3-carbocylic acid ethylester (2.0 g, 8.0 mmol), N-hydroxyphenylimidamide (1.30 g, 9.6 mmol), Na (0.91 g, 40 mmol) in ethanol (50 mL) and toluene (100 mL), in the same manner as illustrated in example 5 to give the title compound (0.66 g, 25%). M.p. 279°–283° C.

Example 9
9-(3-Chloro-1-propyl)-3-(3-phenyl-1,2,4-oxadiazol-5-yl)-9H-β-carboline (Compound 9)

The compound was synthesized by mixing (Compound 8) (0.6 g, 1.9 mmol), 1-bromo-3-chloropropane (0.45 g, 2.9 mmol), NaH (0.09 g, 2.3 mmol) in DMF, in the same manner as illustrated in example 3 to give the title compound (0.72 g, 97%). M.p. 192°–195° C. (and 235.5°–236° C.).

Example 10
1-(3-(3-(3-Phenyl-1,2,4-oxadiazol-5-yl)-9H-β-carbolin-9-yl)-1-propyl)-4-phenylpiperidin-4-ol hydrochloride (Compound 10)

The compound was synthesized by mixing (Compound 9) (0.7 g, 1.8 mmol), 4-phenylpiperidin-4-ol (0.38 g, 2.2 mmol) and TEA (0.55 g, 5.4 mmol) in DMF, in the same manner as illustrated in example 4 to give the title compound (0.47 g, 43%). M.p. 184°–185° C.

Example 11
6-Dimethylsulfamoyl-9H-β-carbolin-3-carboxylic acid ethyl ester (Compound 11)

To chlorosulfonic acid (20 mL), sodium chloride (2.9 g, 49.6 mmol) was carefully added at room temperature. When the evolution of hydrochloride had ceased the resulting mixture was cooled on an ice-bath. 9H-β-Carbolin-3-carboxylic acid ethyl ester (6.0 g, 25 mmol) was slowly added, and the mixture stirred at room temperature for 2 days. The reaction mixture was poured into iced water (100 g). The precipitate was collected and washed with water. This compound was added under stirring to icecold dimethylamine (60% in toluene, 100 mL). The mixture was stirred at 0° C. for an additional 30 min, and at room temperature for 1.5 h. Acetic acid (70 mL) was carefully added (exothermic!). To the resulting mixture was added water (100 mL) and the precipitate filtered, washed with water and dried. This afforded the title compound (3.0 g, 34%). M.p. 310°–311° C.

Example 12
6-Dimethylsulfamoyl-3-(3-ethyl-1,2,4-oxadiazol-5-yl) 9H-β-carboline (Compound 12)

The ester, Compound 11 (10 g, 28.8 mmol) was heated at 100° C., in a mixture of ethanol (200 mL) and KOH (5.5 g, 98.2 mmol), suspended in water (15 mL) for 4 h. Acetic acid was added. The precipitate was washed with water and dried. This afforded the acid (6.8 g, 21.3 mmol). The free acid (2.5 g, 7.8 mmol) was treated as described in example 1 and example 2 to give the title compound (1.3 g, 44%) as a white solid. M.p. 266°–268° C.

Example 13
9-(3-Chloro-1-propyl)-6-dimethylsulfamoyl-3-(3-ethyl-1,2,4-oxadiazol-5-yl)-9H-β-carboline (Compound 13)

The compound was synthesized by mixing (Compound 12) (3.0 g, 8.8 mM), NaH (0.46 g, 11.0 mmol) and 1-bromo-3-chloropropane ( 1.5 g, 9.7 mmol) in DMF, in the same manner as illustrated in example 3 to give the title compound (0.25 g, 7%). M.p. 223°–224° C.

Example 14
1-(3-(3-(3-Ethyl-1,2,4-oxadiazol-5-yl)-6-dimethylsulfamoyl-9H-β-carbolin-9-yl)-1-5 propyl)-4-phenylpiperidin-4-ol hydrochloride (Compound 14)

The compound was synthesized by mixing (Compound 13) (0.25 g, 0.64 mmol), 4-phenylpiperidin-4-ol (0.136 g, 0.77 mmol) and TEA (0.19 g, 1.9 mmol) in DMF, in the same manner as illustrated in example 4 to give the title compound (0.09 g, 21%). M.p. 186°–189° C.

Example 15
6-Nitro-9H-β-carboline-3-carboxylic acid ethyl ester (Compound 15)

9H-β-carboline-3-carboxylic acid ethyl ester (20 g, 833 mmol) was slowly added to concentrated nitric acid (400 mL). The reaction mixture was stirred at 70°–75° C. for 2 h. After cooling to room temperature the resulting mixture was poured onto ice (1 kg). The precipitated compound was collected, and recrystallized from pyridine (650 mL). This afforded the title compound (14.9 g, 63%). M.p. 339°–341° C.

Example 16
6-Amino-9H-β-carboline-3-carboxylic acid ethyl ester (Compound 16)

A suspension of Pd (10% on carbon, 1.0 g), and Compound 15 (8.0 g, 28 mmol) in anhydrous ethanol (300 mL) was hydrogenated (2280 mL) at 1 atm. The reaction mixture was filtered through a filter aid. The filtrate was concentrated in vacuo to give the title compound (5.62 g, 79%). M.p. 226°–228° C.

Example 17
6-Dipropenylamino-9H-β-carboline-3-carboxylic acid ethyl ester (Compound 17)

To a solution of Compound 16 (15.8 g, 62 mmol) in anhydrous ethanol (300 mL), allylbromide (8.4 g, 69.4 mmol) and TEA (20 mL) were added. The reaction mixture was stirred under a nitrogen atmosphere at 80° C. for 2 h. Additionally allylbromide (8.4 g, 69.4 mmol) and TEA (12 mL) were added, and stirring continued at 80° C. for 48 h. The reaction mixture was concentrated in vacuo, and the residual oil was poured into water (300 mL). The solid was filtered and dried, to give the title compound (16.5 g, 80%). M.p. 235°–238° C.

Example 18
6-Dipropenylamino-3-(3-ethyl-1,2,4-oxadiazol-5-yl)-9H-β-carboline (Compound 18)

The compound was synthesized by mixing Na (2.6 g, 114 mmol) dissolved in ethanol (200 mL), (Compound 17) (13.2 g, 38 mmol), N-hydroxypropylimidamide (5.1 g, 57 mmol) in toluene, in the same manner as illustrated in example 5 to give the title compound (4.4 g, 32%). M.p. 151°–156° C.

Example 19
9-(3-Chloro-1-propyl)-6-dipropenylamino-3-(3-ethyl-1,2,4-oxadiazol-5-yl)-9H-β-carboline (Compound 19)

The compound was synthesized by mixing (Compound 18) (1 g, 2.8 mmol), NaH (50% in oil) (0.075 g, 3.1 mmol) and 1-bromo-3-chloropropane (0.44 g, 3.1 mmol) in DMF in the same manner as illustrated in example 3 to give the title compound (0.35 g, 28%).

The $^1$H-NMR in (CDCl$_3$): 1.45 (t,3H), 2.35 (t,2H), 2,9 (q,2H), 3.5 and 3.35 (t,t,additional 2H), 4.0 (d,4H), 4.5 (t,2H), 5.25 (2d,4H), 5.95 (m,2H), 7.15 (d, 1H), 7.4 (s and d,2H), 8.7 (s,1H), 9.0 (s,1H).

Example 20

1-(3-(3-(3-Ethyl-1,2,4-oxadiazol-5-yl)-6-dipropenylamino-9H-β-carbolin-9-yl)-1-propyl-4-phenylpiperidin-4-ol hydrochloride (Compound 20)

The compound was synthesized by mixing (Compound 19) (0.35 g, 0.8 mmol), 4-phenylpiperidin-4-ol (0.14 g, 0.8 mmol) and TEA (0.32 g, 3.2 mmol) in the same manner as illustrated in example 4 to give the title compound (0.33 g, 60%). M.p. 133°–139° C. (dec.).

Example 21

6-Dimethylamino-β-carboline-3-carboxylic acid ethyl ester (Compound 21)

To a solution of compound 16 (1.00 g, 0.0039 mol) in CH$_3$CN (30 mL) were added 35% formaldehyde (aq) (3.4 mL, 0.0392 mol) and acetic acid (0.4 mL). The mixture was stirred at room temperature for 2 h, and methanol (20 mL) and NaBH$_4$ (0.74 g, 0.0117 mol) were added. After stirring for an additional 15 min. at room temperature the solvent as removed in vacuo from the reaction mixture, and the residue dissolved in 1M KOH (20 mL), and the resulting solution extracted with CH$_2$Cl$_2$ (100 mL). The organic phase was washed with 1M KOH (2×20 mL) and dried (MgSO$_4$). The solvent was removed in vacuo to give the title compound 0.76 g (69%). M.p. 220°–221° C.

Example 22

6-Dimethylamino-3-(3-ethyl-1,2,4-oxadiazol-5-yl)-β-carboline (Compound 22)

Sodium (0.11 g, 0.0048 mol) was carefully added to absolute ethanol (100 mL). To the sodium ethoxide solution were added compound 21 (0.53 g, 0.0019 mol), propionamide oxime (0.20 g, 0.0022 mol) and toluene (150 mL). The resulting mixture was heated at reflux temperature and the water removed from the mixture by azeotropic distillation. The solvent was removed from the reaction in vacuo, and the residue washed with water until neutral pH, and dried in vacuo to give the title compound 0.25 g (43%). M.p. 235°–240° C.

Example 23

9-(3-Chloro-1-propyl)-6-dimethylamino-3-(3-ethyl-1,2,4-oxadiazol-5-yl)-β-carboline (Compound 23)

To a solution of compound 22 (0.25 g, 0.0009 mol) in anhydrous DMF (30 mL) was added 50% sodium hydride in mineral oil (0.05 g, 0.0012 mol). The mixture was stirred for 30 min. at room temperature, and then added to a solution of 1-bromo-3-chloropropane (0.15 g, 0.001 mol) in anhydrous DMF (50 mL). The resulting mixture was stirred at ambient temperature over night, and the product then precipitated by the addition of water. The crude product was purified on a silica gel column (Eluent: CH$_2$Cl$_2$/methanol (9:1)) to give the title compound 0.22 g (65%). M.p. 183°–186° C.

Example 24

1-(3-(3-Ethyl-1,2,4-oxadiazol-5-yl)-6-dimethylamino-β-carbolin-9-yl)-1-propyl)-4-phenylpiperidin-4-ol hydrochlorid (Compound 24)

A solution of compound 23 (0.22 g, 0.0008 mol), TEA (0.32 g, 0.003 mol) and 4-phenylpiperidin-4-ol (0.17 g, 0.0009 mol) in anhydrous DMF was stirred at room temperature for 96 h. The reaction mixture was filtered and the solvent was removed in vacuo. The residue was purified on a silica gel column (Eluent: CH$_2$Cl$_2$/methanol (9:1)). The product was acidified with 2M HCl(g) in diethyl ether, to give the title compound 0.08 g (16%). M.p. 199°–201° C.

Example 25

9-(3-Chloro-1-propyl)-3-(3-methyl-1,2,4-oxadiazol-5-yl)-β-carboline (Compound 25)

To a solution of 3-(3-methyl-1,2,4-oxadiazol-5-yl)-β-carboline (2.00 g, 0.008 mol) in anhydrous DMF (50 mL) was added 50% sodium hydride in mineral oil (0.42 g, 0.01 mol). The mixture was stirred for 1 h at room temperature, and then carefully added to a solution of 1-bromo-3-chloropropane (1.39 g, 0.0088 mol) in anhydrous DMF (150 mL). The resulting mixture was stirred at ambient temperature over night. The reaction mixture was concentrated in vacuo, and the crude product was purified on a silica gel column (Eluent: CH$_2$Cl$_2$/methanol (9:1)) to give the title compound 2.11 g (81%). M.p. 180°–185° C.

Example 26

1-(3-(3-Methyl-1,2,4-oxadiazol-5-yl)-β-carbolin-9-yl)-1-propyl)-4-phenylpiperidin-4-ol hydrochloride (Compound 26)

A solution of compound 25 (1.00 g, 0.0031 mol), TEA (1.25 g, 0.0124 mol) and 4-phenylpiperidin-4-ol (0.60 g, 0.0034 mol) in anhydrous DMF (50 mL) was stirred at room temperature overnight, and then heated at 80° C. for 6 h. The reaction mixture was filtered and the solvent was removed in vacuo. The residue was purified on a silica gel column (Eluent: CH$_2$Cl$_2$/methanol (9:1)). The product was acidified with 2M HCl(g) in diethyl ether, to give the title compound 0.69 g (44%). M.p. 179.5°–180.5° C.

Example 27

9-(3-Chloro-1-propyl)-3-(5-methyl-1,2,4-oxadiazol-3-yl)-β-carboline (Compound 27)

To a solution of 3-(5-methyl-1,2,4-oxadiazol-3-yl)-β-carboline (0.25 g, 0.001 mol) in anhydrous DMF (30 mL) was added 50% sodium hydride in mineral oil (0.03 g, 0.0011 mol). The mixture was stirred for 1 h at room temperature, and then carefully added to a solution of 1-bromo-3-chloropropane (0.17 g, 0.0011 mol) in anhydrous DMF (20 mL). The resulting mixture was stirred at ambient temperature for 96 h. The reaction mixture was concentrated in vacuo, and the crude product was purified twice on a silica gel column 1) (Eluent: CH$_2$Cl$_2$/methanol (9:1)); 2) (Eluent: ethyl acetate/toluene (1:1)) to give the title compound 0.21 g (64%). M.p. 130°–135° C.

Example 28

1-(3-(5-Methyl-1,2,4-oxadiazol-3-yl)-β-carbolin-9-yl)-1-propyl)-4-phenylpiperidin-4-ol hydrochloride (Compound 28)

A solution of compound 27 (0.21 g, 0.0007 mol), TEA (0.26 g, 0.0003 mol) and 4-phenylpiperidin-4-ol (0.11 g, 0.0007 mol) in anhydrous DMF (30 mL) was stirred at 50° C. for 5 d. The reaction mixture was filtered and the solvent was removed in vacuo. The residue was purified on a silica gel column (Eluent: CH$_2$Cl$_2$/methanol/25% NH$_4$OH (aq) (90:9:1)). The product was acidified with 2M HCl(g) in diethyl ether, to give the title compound 0.15 g (43%). M.p. decomposes at 157°–159° C.

We claim:
1. A compound of formula I

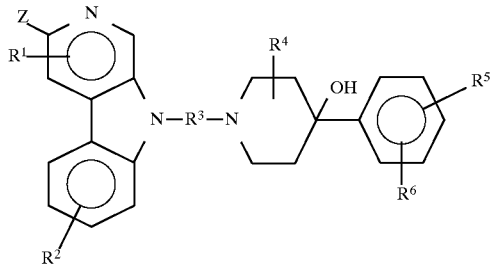

wherein
$R^1$ and $R^2$ independently are hydrogen, halogen, hydroxy, nitro, $(CH_2)_n-(C=O)-(CH_2)_m CH_3$, $-NR^9 R^{10}$, $-SONR^{11}R^{12}$, $-COOR^{13}$, $-CONR^{14}R^{15}$, $C_{1-6}$-alkyl, $C_{1-6}$-alkoxy, trifluoromethyl or trifluoromethoxy wherein $R^9$, $R^{10}$, $R^{11}$, $R^{12}$, $R^{13}$, $R^{14}$ and $R^{15}$ independently are hydrogen, $C_{1-6}$-alkyl, $C_{2-6}$-alkenyl or $C_{2-6}$-alkynyl, and wherein n and m independently are 0, 1, 2, 3 or 4; and $R^3$ is $C_{1-5}$-alkylene optionally substituted with one or two $C_{1-6}$-alkyl or $C_{2-5}$-alkenylene or $C_{2-5}$-alkynylene or

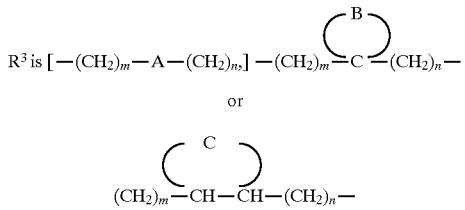

wherein B is $C_{1-5}$-alkylene and C is $C_{1-5}$-alkylene and m and n independently are 0, 1 or 2; and $R^4$ is hydrogen or $C_{1-6}$-alkyl; and $R^5$ and $R^6$ independently are hydrogen, halogen, hydroxy, nitro, $-NR^{16}R^{17}$, $-COOR^{18}$, $C_{1-6}$-alkyl, $C_{1-6}$-alkoxy, trifluoromethyl or trifluoromethoxy wherein $R^{16}$, $R^{17}$ and $R^{18}$ independently are hydrogen, $C_{1-6}$-alkyl, $C_{2-6}$-alkenyl or $C_{2-6}$-alkynyl; and Z is

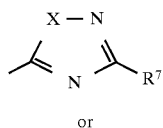

or

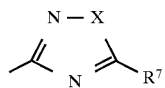

wherein X is oxygen or sulphur; and $R^7$ is hydrogen, $C_{1-6}$-alkyl, $C_{2-6}$-alkenyl, $C_{2-6}$-alkynyl, phenyl, $C_{3-7}$-cycloalkyl, $-OR^8$ or $-SR^8$ wherein $R^8$ is hydrogen or $C_{1-6}$-alkyl; or a pharmaceutically acceptable salt thereof.

2. The compound according to claim 1 which is
1-(3-(3-(3-Ethyl-1,2,4-oxadiazol-5-yl)-9H-β-carbolin-9-yl)-1-propyl)-4-phenylpiperidin-4-ol,
1-(3-(3-(3-Cyclopropyl-1,2,4-oxadiazol-5-yl)-9H-β-carbolin-9-yl)-1-propyl)-4-phenylpiperidin-4-ol,
1-(3-(3-(3-Phenyl-1,2,4-oxadiazol-5-yl)-9H-β-carbolin-9-yl)-1-propyl)-4-phenylpiperidin-4-ol,
1-(3-(3-(3-Ethyl-1,2,4-oxadiazol-5-yl)-6-dimethylsulfamoyl-9H-β-carbolin-9-yl)-1-propyl)-4-phenylpiperidin-4-ol,
1-(3-(3-(3-Ethyl-1,2,4-oxadiazol-5-yl)-6-dipropenylamino-9H-β-carbolin-9-yl)-1-propyl)-4-phenylpiperidin-4-ol,
or a pharmaceutically acceptable salt thereof.

3. A pharmaceutical composition comprising as active component a compound according to claim 1 together with a pharmaceutically acceptable carrier or diluent.

4. A pharmaceutical composition suitable for treating a central nervous system ailment related to the inhibition of GABA uptake via the GAT-4 subtype carrier comprising an effective amount of a compound according to claim 1 together with a pharmaceutically acceptable carrier or diluent.

5. The pharmaceutical composition according to claim 4 comprising between 0.5 mg and 1000 mg of the compound according to claim 1 per unit dose.

6. A method of treating a central nervous system ailment related to the inhibition of GABA uptake via the GAT-4 subtype carrier in a subject in need of such treatment comprising administering to said subject an effective amount of a compound according to claim 1.

7. A method of treating a central nervous system ailment related to the inhibition of GABA uptake via the GAT-4 subtype carrier in a subject in need of such treatment comprising administering to said subject a pharmaceutical composition according to claim 4.

* * * * *

UNITED STATES PATENT AND TRADEMARK OFFICE
CERTIFICATE OF CORRECTION

PATENT NO. : 5,834,482
DATED : October 21, 1997
INVENTOR(S) : Jane Marie Lundbeck, et al.

It is certified that error appears in the above-indentified patent and that said Letters Patent is hereby corrected as shown below:

Col. 5, line 66    change "1000g and
                   insert --1.000xg --

Col. 9, line 8     change "illusterated"
                   insert --illustrated"

Col. 13, line 29   delete "$R^3$ is $[-(CH_2)_m-A-(CH_2)_{n'}]-(CH_2)_m-\overset{(B)}{C}-(CH_2)_n-$ and insert -- $R^3$ is $-(CH_2)_m-A-(CH_2)_{n'}-(CH_2)_m-\overset{(B)}{C}-(CH_2)_n$ Signed and Sealed this Fifth Day of October, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,834,482

DATED : October 21, 1997

INVENTOR(S) : Lundbeck et al.

It is certified that error appears in the above-identified patent and that said Letters Patent is hereby corrected as shown below:

Col. 13, line 29  delete "$R^3$ is $[-(CH_2)_m-A-(CH_2)_{n'}]-(CH_2)_m-\overset{B}{\underset{}{C}}-(CH_2)_n-$ and insert -- $R^3$ is $-(CH_2)_m-\overset{B}{\underset{}{C}}-(CH_2)_n$ Signed and Sealed this First Day of February, 2000

Attest:

Attesting Officer

Q. TODD DICKINSON

Acting Commissioner of Patents and Trademarks